US009526867B2

(12) United States Patent
Lichtenstein

(10) Patent No.: US 9,526,867 B2
(45) Date of Patent: Dec. 27, 2016

(54) MULTISHAPE CATHETER

(71) Applicant: BIOSENSE WEBSTER (ISRAEL), LTD., Yokneam (IL)

(72) Inventor: Yoav Lichtenstein, Raanana (IL)

(73) Assignee: BIOSENSE WEBSTER (ISRAEL), LTD., Yokneam (IL)

(*) Notice: Subject to any disclaimer, the term of this patent is extended or adjusted under 35 U.S.C. 154(b) by 687 days.

(21) Appl. No.: 13/956,621

(22) Filed: Aug. 1, 2013

(65) Prior Publication Data
US 2015/0038900 A1 Feb. 5, 2015

(51) Int. Cl.
*A61M 39/10* (2006.01)
*A61M 25/01* (2006.01)
*A61M 25/00* (2006.01)
*A61B 5/042* (2006.01)
*A61B 5/06* (2006.01)

(52) U.S. Cl.
CPC ..... *A61M 25/0155* (2013.01); *A61M 25/0041* (2013.01); *A61M 25/0045* (2013.01); *A61M 25/0102* (2013.01); *A61M 25/0152* (2013.01); *A61B 5/0422* (2013.01); *A61B 5/062* (2013.01); *A61M 2025/0024* (2013.01); *Y10T 29/49002* (2015.01)

(58) Field of Classification Search
CPC ................ A61M 2025/0024; A61M 25/0152; A61M 39/10
USPC ...................... 604/95.04, 523, 536
See application file for complete search history.

(56) References Cited

U.S. PATENT DOCUMENTS

| 4,935,017 | A | 6/1990 | Sylvanowicz |
| 5,569,221 | A | 10/1996 | Houser et al. |
| 7,419,477 | B2 | 9/2008 | Simpson et al. |
| 8,313,478 | B2 | 11/2012 | Tockman et al. |
| 8,323,171 | B2 | 12/2012 | Lebovic et al. |
| 8,326,423 | B2 | 12/2012 | Zhu et al. |
| 2009/0157162 | A1 | 6/2009 | Chow et al. |
| 2011/0264057 | A1 | 10/2011 | Eversull et al. |
| 2012/0109079 | A1 | 5/2012 | Asleson et al. |

FOREIGN PATENT DOCUMENTS

WO WO 98/50098 A1 11/1998
WO WO 2011/140586 A1 11/2011

OTHER PUBLICATIONS

European Search Report for corresponding Application No. EP14179230 dated Feb. 13, 2015.

*Primary Examiner* — Deanna K Hall

(57) ABSTRACT

A probe, consisting of a flexible insertion tube, for insertion into a subject via a body lumen. The probe includes a sequence of tubular modules contained within the insertion tube, each module having a rigid tube segment having a preset shape and containing internal grooves on an interior surface of the tube segment. The probe further includes a flexible expander tube, which is threaded through the sequence of tubular modules and has external grooves configured to engage the internal grooves within the tube segment of each of the tubular modules when the expander tube is expanded, so as to hold the tubular modules in mutual alignment, wherein the tubular modules are able to move out of mutual alignment when the expander tube is unexpanded. The probe also has an expansion element, which is insertable through the flexible expander tube so as to expand the expander tube.

8 Claims, 8 Drawing Sheets

MULTISHAPE CATHETER

FIELD OF THE INVENTION

The present invention relates generally to probes or catheters, and specifically to probes having a variable shape.

BACKGROUND OF THE INVENTION

U.S. Pat. No. 7,419,477, to Simpson, et al., whose disclosure is incorporated herein by reference, describes a method of catheterization using a catheter having a distal region that includes a shapeable region. The method includes imparting a pre-established shape to the shapeable region.

U.S. Pat. No. 8,323,171, to Lebovic, et al., whose disclosure is incorporated herein by reference, describes a flexible implantable brachytherapy treatment device for delivering brachytherapy to a target tissue region of a human or other mammalian body. The device may include one or more one or more radiation sources fixed relative to a non-dissolving casing.

U.S. Patent Application 2012/0109079, to Asleson, et al., whose disclosure is incorporated herein by reference, describes a trans-septal catheter delivery system having an elongate first tubular member and an elongate second tubular member receivable within the first tubular member. The first tubular member includes an adjustable portion adjacent a distal end.

U.S. Pat. No. 8,326,423, to Zhu, et al., whose disclosure is incorporated herein by reference, describes a system for steering electrical stimulation in cardiac rhythm management. A catheter arrangement includes an elongated structure supporting a fixation mechanism used to attach the arrangement to heart tissue.

U.S. Pat. No. 8,313,478, to Tockman, et al., whose disclosure is incorporated herein by reference, describes a catheter assembly comprising an outer catheter member and an inner catheter member. The inner catheter member is slidably and rotatably disposed within the lumen of the outer catheter member. The outer catheter member has a distal end portion having a pre-formed curvature.

U.S. Pat. No. 4,935,017, to Sylvanowicz, whose disclosure is incorporated herein by reference, describes a catheter assembly by which a curved configuration at a distal portion of a catheter can be varied. The catheter has a predetermined curve at its distal end, and a sheath can be advanced over the distal end that tends to straighten the curve.

PCT Application PCT/AU2011/000532, to Ogle, whose disclosure is incorporated herein by reference, describes a catheter shape adjusting mechanism. A catheter includes a stylet having a shaped distal part received within a catheter sheath. The catheter includes a stylet carrier displaceably carried by a handle and a shape adjuster in the form of a collar rotatable about the handle.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a probe, including:

a flexible insertion tube, which is configured for insertion into a body of a subject via a body lumen;

a sequence of tubular modules, which are contained within the insertion tube, each module including a rigid tube segment having a respective preset shape and containing internal grooves on an interior surface of the tube segment;

a flexible expander tube, which is threaded through the sequence of the tubular modules and has external grooves configured to engage the internal grooves within the tube segment of each of the tubular modules when the expander tube is expanded, so as to hold the tubular modules in mutual alignment, wherein the tubular modules are able to move out of the mutual alignment when the expander tube is unexpanded; and an expansion element, which is insertable through the flexible expander tube so as to expand the expander tube.

Typically, the mutual alignment of the tubular modules forms a predetermined shape for the probe.

In a disclosed embodiment the flexible insertion tube includes channels configured to accommodate at least one of cabling and fluid.

In a further disclosed embodiment the probe has at least one electrode, configured to acquire signals from the body of the subject, formed on the flexible insertion tube.

In a yet further disclosed embodiment the respective preset shape includes at least one of a right cylinder and an elbow.

In an alternative embodiment the respective preset shape has an axis, and is terminated by a pair of plane faces orthogonal to the axis.

In a further alternative embodiment the expansion element includes a wire.

In a yet further alternative embodiment the expansion element includes a fluid.

There is further provided, according to an embodiment of the present invention embodiment of the present invention, a method for forming a probe, including:

configuring a flexible insertion tube for insertion into a body of a subject via a body lumen;

introducing a sequence of tubular modules into the insertion tube, each module including a rigid tube segment having a respective preset shape and containing internal grooves on an interior surface of the tube segment;

threading a flexible expander tube through the sequence of the tubular modules, the flexible expander tube having external grooves configured to engage the internal grooves within the tube segment of each of the tubular modules when the expander tube is expanded, so as to hold the tubular modules in mutual alignment, wherein the tubular modules are able to move out of the mutual alignment when the expander tube is unexpanded; and inserting an expansion element into the flexible expander tube so as to expand the expander tube.

The present disclosure will be more fully understood from the following detailed description of the embodiments thereof, taken together with the drawings, in which:

DETAILED DESCRIPTION OF EMBODIMENTS

Overview

Figure 1:
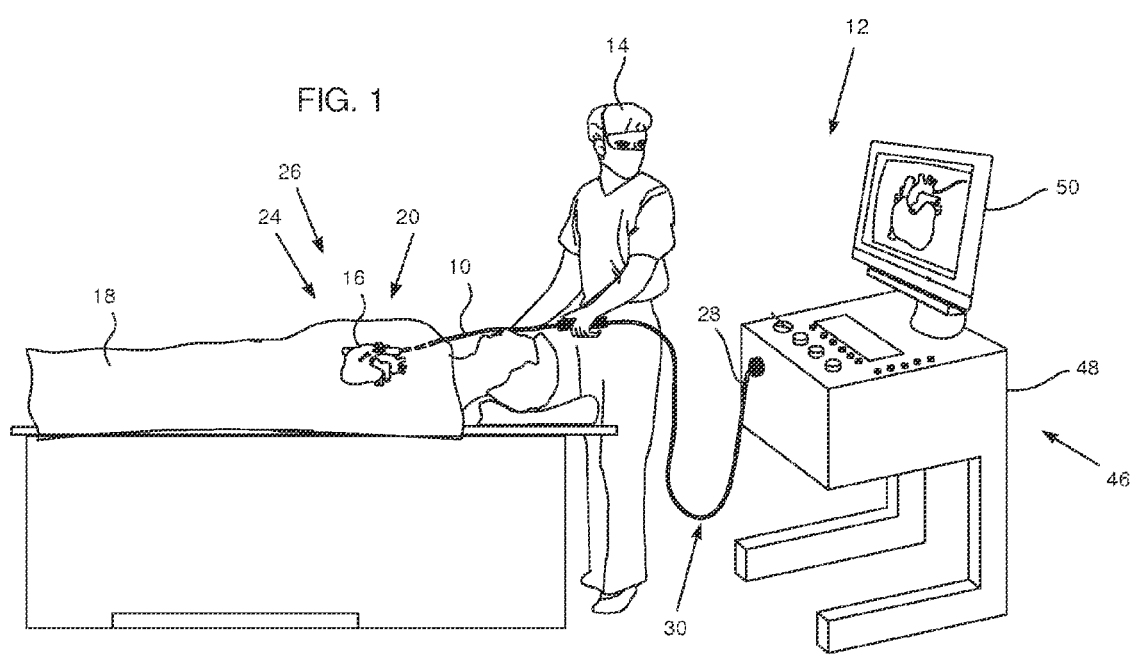
FIG. 1 is a schematic illustration of an invasive medical procedure using a multishape catheter, according to an embodiment of the present invention.

An embodiment of the present invention provides a system whereby a probe, typically the distal end of the probe, may be formed into substantially any two or three-dimensional predetermined shape. The probe is formed of a sequence of rigid tubular modules having preset shapes, typically right cylinders and/or elbows of differing angles. Each module has internal grooves on the internal surface of the module. The modules act as the "skeleton" of the probe, and a sequence of the modules may be threaded onto a flexible expander tube, in an unexpanded state, which has external grooves on an external surface of the tube. The threaded sequence of modules is then inserted into a flexible insertion tube, which acts as an outer sleeve of the probe. At this stage the modules may move with respect to each other, since the expander tube is in its unexpanded state.

To lock the modules into the predetermined shape, an expansion element, typically a wire, is inserted into the expander tube. The insertion causes the tube to expand, so that the external grooves of the tube engage with internal grooves of the modules. The engagement causes the modules to lock, or be held, in mutual alignment with each other, and during the insertion the alignment between adjacent modules, which typically butt against each other, may be adjusted to achieve the predetermined shape. During the insertion, if necessary adjacent modules may be moved out of alignment by "unexpanding" the expander tube, after which a new mutual alignment may be achieved by reengaging the two sets of grooves by re-expanding the insertion tube.

Embodiments of the present invention enable substantially any shape for a probe to be constructed by selection of an appropriate sequence of rigid tubular modules.

While the modules are rigid, they are typically sufficiently flexible, or bendable, to enable insertion of the constructed probe into a lumen of a patient. Once free of the lumen, for example within a body cavity such as a chamber of the heart, the modules return or "spring back" to their initial unbent shape, so that the predetermined shape of the probe is recovered.

System Description

In the following description, like elements in the drawings are identified by like numerals, and the like elements are differentiated as necessary by appending a letter to the identifying numeral.

FIG. 1 is a schematic illustration of an invasive medical procedure using a multishape catheter 10, according to an embodiment of the present invention embodiments of the present invention. By way of example, catheter 10, also referred to herein as probe 10, is assumed to be part of an apparatus 12 used for an invasive medical procedure, performed by a medical professional 14, on a myocardium 16 of the heart of a human patient 18. The medical procedure comprises measurements of electropotentials of the heart at multiple locations 20, locations 20A, 20B, . . . , of the myocardium. In order to perform the measurements, professional 14 inserts probe 10 into a lumen of the patient, so that a distal end 24 of the probe enters the heart of the patient. In order to measure the electropotentials, distal end 24 comprises electrodes 26 mounted on the outside of catheter 10, the electrodes contacting respective regions of the myocardium. Catheter 10 has a proximal end 28.

Apparatus 12 is controlled by a system processor 46, which is located in an operating console 48 of the apparatus. During the procedure, processor 46 typically tracks a location and an orientation of distal end 24 of the catheter, using any method known in the art. For example, processor 46 may use a magnetic tracking method, wherein magnetic transmitters external to patient 18 generate signals in coils positioned in the distal end. The Carto® system produced by Biosense Webster, of Diamond Bar, Calif., uses such a tracking method.

Signals derived from electropotentials acquired by electrodes 26, due to electrode contact with the heart, are transferred back via cabling 30 in catheter 10 to processor 46. The processor may analyze the received signals, and may present results of the analysis on a screen 50 attached to the console. The results derived from the analysis typically include maps of electrical characteristics of the heart such as local activation times, numerical displays, and/or graphs of the electropotentials vs. time.

The software for processor 46 may be downloaded to the processor in electronic form, over a network, for example. Alternatively or additionally, the software may be provided on non-transitory tangible media, such as optical, magnetic, or electronic storage media.

Prior to inserting distal end 24 into patient 18, professional 14 assembles distal end 24 into a preset configuration required by the professional. The assembly uses elements incorporated into the distal end that are described in detail below. As will be apparent the construction of distal end 24 enables the distal end to be configured to follow substantially any three-dimensional (3D) linear path. Examples of such paths include a "C" path, an "S" path, a "W" path, deformations of these paths into 3D paths, and other 3D paths such as a helix. The preset configuration selected by the professional typically depends on the available access to the heart of patient 18, as well as depending on the regions of myocardium 16 the professional desires to measure.

While the description herein assumes for simplicity that it is the distal end of catheter 10 that is constructed into a preset configuration, the scope of the present invention includes construction of substantially any section of catheter 10 into a preset configuration, the sections including proximal end 28 and sections intermediate the proximal and distal ends of the catheter.

Figure 2:
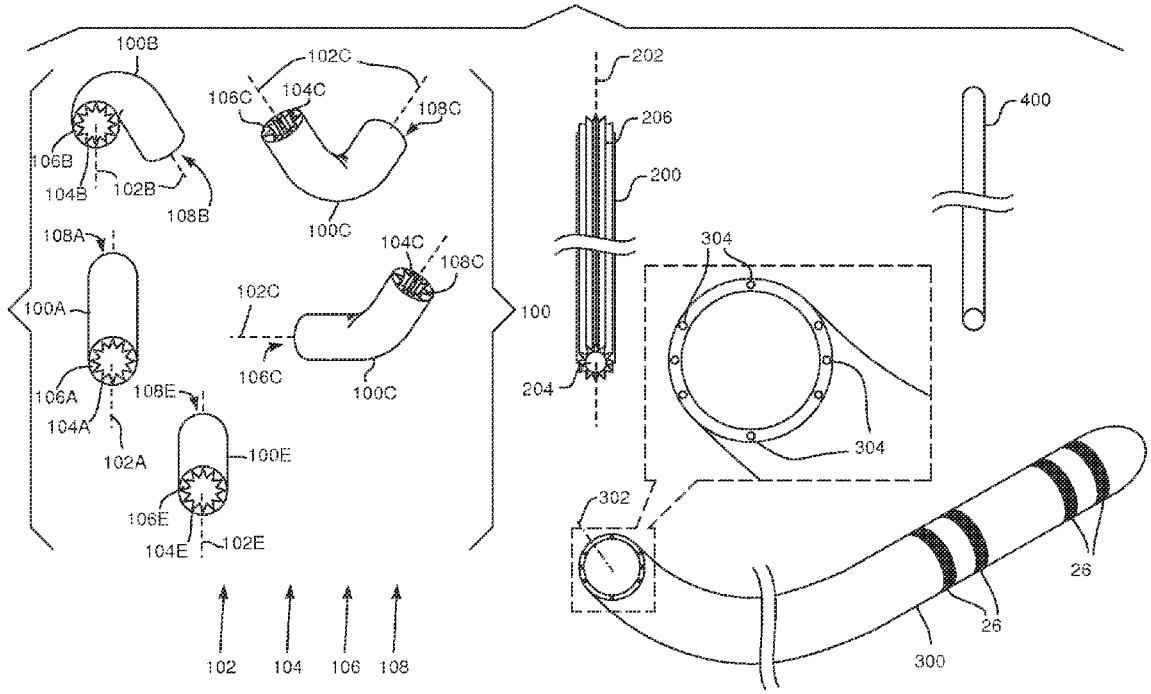
FIG. 2 shows schematic views of portions of a distal end of the catheter, according to an embodiment of the present invention.

FIG. 2 shows schematic views of portions of distal end 24, according to an embodiment of the present invention. As stated above, distal end 24 is assembled prior to being introduced into the heart of patient 18, and the assembled distal end is comprised of a number of separate parts, illustrated in FIG. 2.

Referring to FIG. 2, distal end 24 is composed of a multiplicity of tubular modules 100, which are rigid tube segments having a number of different preset shapes. Typically, tubular modules 100 are preset into the form of right cylinders and elbows. In the disclosure and in the claims, an elbow is assumed to be a "bent" right cylinder, i.e., a right cylinder which has been deformed so that its axis is no longer a straight line. Typically, the axis of an elbow is a section of a circle. Each tubular module has a respective axis 102, the axis of the right cylinders corresponding to an axis of symmetry of the cylinder, and the axis of a particular elbow corresponds to the axis of the corresponding right cylinder after the cylinder, with its axis, has been bent. Typical angles of the elbows are 90°, although angles such as 45° or 60°, or any other convenient value are included within the scope of the present invention.

Each tubular module 100 has a circular outer cross-section, as measured orthogonally to the respective axis of the element, so that external walls of each element are smooth. In contrast, internal walls of each tubular module are grooved with grooves 104, the grooves being parallel to the axis of the element. Typically, grooves 104 are symmetrically distributed with respect to the axis, so that an inner cross-section of each tubular element has the shape of a symmetrical reentrant polygon or star.

Each tubular module 100 terminates in a pair of plane faces 106, 108, that are orthogonal to the element axis.

In one embodiment the tubular modules are formed from polyimide plastic.

As stated above, tubular modules 100 may have different preset shapes. Illustrated in FIG. 2, as examples of modules 100, are:

A first right cylinder tubular module 100A having an axis 102A, and grooves 104A on the internal wall of the module. Module 100A terminates in plane faces 106A and 108A;

A 90° elbow tubular module 100B having an axis 102B and grooves 104B on the internal wall of the module. The elbow terminates in plane faces 106B and 108B;

Another 90° elbow tubular module 100C having an axis 102C and grooves 104C on the internal wall of the module. This elbow terminates in plane faces 106C and 108C; and A 60° elbow tubular module 100D having an axis 102D and grooves 104D on the internal wall of the module. The 60° elbow terminates in plane faces 106D and 108D; and A second right cylinder tubular module 100E having an axis 102E, and grooves 104E on the internal wall of the module. Module 100E is shorter than module 100A, and terminates in plane faces 106E and 108E.

Distal end 24 comprises a flexible expander tube 200, which has an axis of symmetry 202 and an inner cross-section measured orthogonal to the axis that is circular. (In this case an inner wall 204 of the tubing is relatively smooth.) As described in more detail below, in construction of catheter 10, tube 200 is threaded through a sequence of tubular modules 100. An outer wall of the tubing has grooves 206 parallel to axis 202. The grooves of expander tube are configured to mate, when tube 200 is expanded, with the grooves of modules 100, so that in its expanded or unexpanded state a cross-section of grooves 206 taken orthogonally to axis 202 is a symmetrical reentrant polygon similar to the reentrant polygon of the tubular modules.

In one embodiment, expander tube 200 is formed from nylon.

Distal end 24 comprises a flexible insertion tube 300, which has an axis of symmetry 302, and which is biocompatible so as to be insertable into patient 18. Tube 300 acts as a containing sleeve for tubular modules 100. Tube 300 has channels 304 within the tube, the channels being configured to accommodate cabling for transferring signals between distal end 24 and proximal end 28 of catheter 10. Alternatively or additionally, channels 304 may transfer fluid, such as irrigation fluid, between the proximal and distal ends of catheter 10. As illustrated in FIG. 2, tube 300 has electrodes 26 on the outside of the tube. The electrodes are connected to conductive cabling within channels 304, and signals acquired from the myocardium of patient 18 by the electrodes are conveyed via the cabling to processor 46.

In some embodiments distal end 24 comprises an expansion wire 400 which on insertion into flexible expander tube 200 causes the tube to expand. Other systems for expanding tube 200 are described below. The expansion of tube 200 from its unexpanded state causes grooves 206 of tube 200 to engage with grooves 102 of tubular modules 100. As is explained in more detail below, the engagement causes an alignment of modules 100 to be held or locked in place, so that when implemented in forming probe 10, the engagement transfers the probe from an unlocked to a locked state. Similarly, return of tube to its unexpanded state disengages grooves 206 from grooves 102, so causing the modules to unlock and move out of their alignment.

Figure 3:
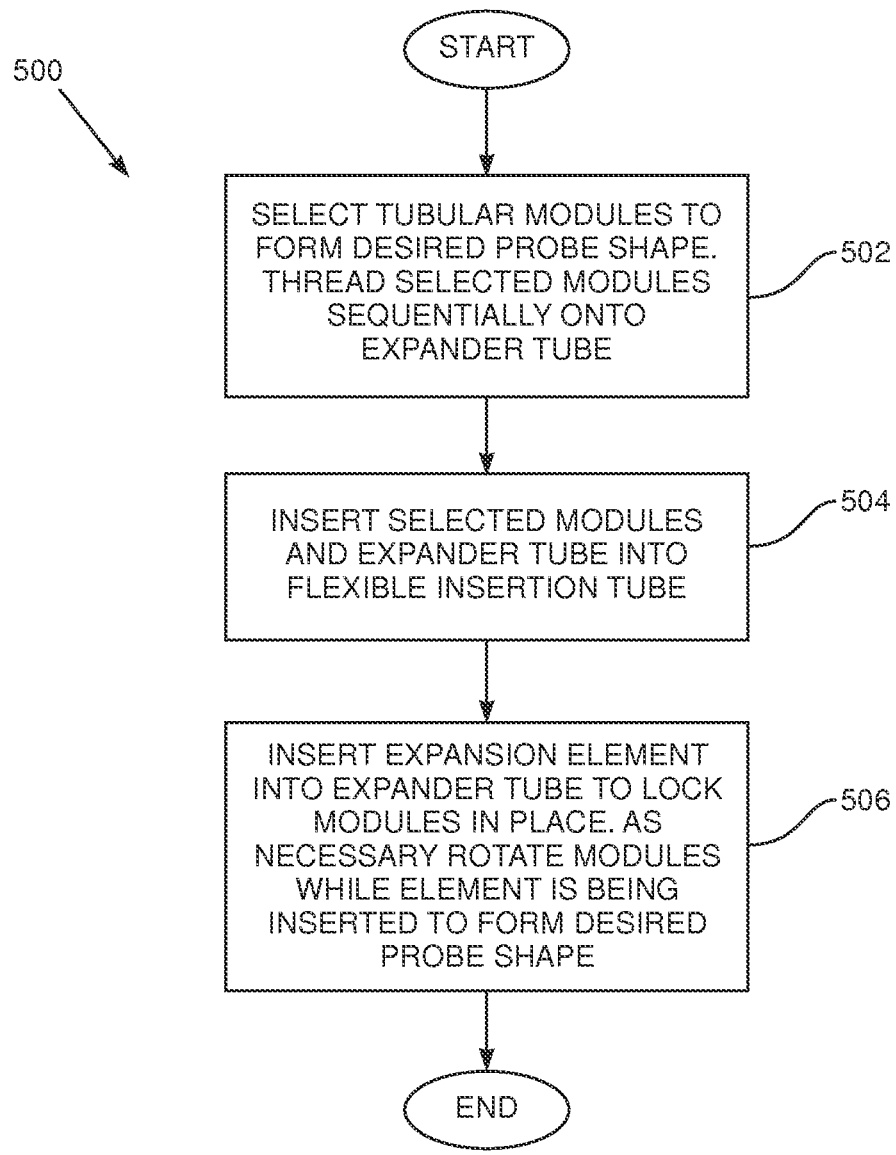
FIG. 3 is a flowchart showing steps performed in constructing a catheter, according to an embodiment of the present invention.

FIG. 3 is a flowchart 500 showing steps performed in constructing probe 10, according to an embodiment of the present invention. The description of the flowchart assumes for simplicity that probe 10 is inserted into patient 18 to measure electrical signals in the heart of the patient, and those having ordinary skill in the art will be able to adapt the description for other types of probe insertion into the patient.

In an initial step 502, professional 14 selects tubular modules 100 so that the modules, when butted together at their respective plane faces, form a shape desired by the professional. The desired shape, also herein termed the predetermined shape, corresponds to the shape of the completed probe, and is typically chosen by the professional according to the access available to the heart of patient 18, as well as according to the locations within the heart where the professional desires to make measurements. As the tubular modules are selected, they are threaded sequentially onto flexible expander tube 200.

Figure 4:
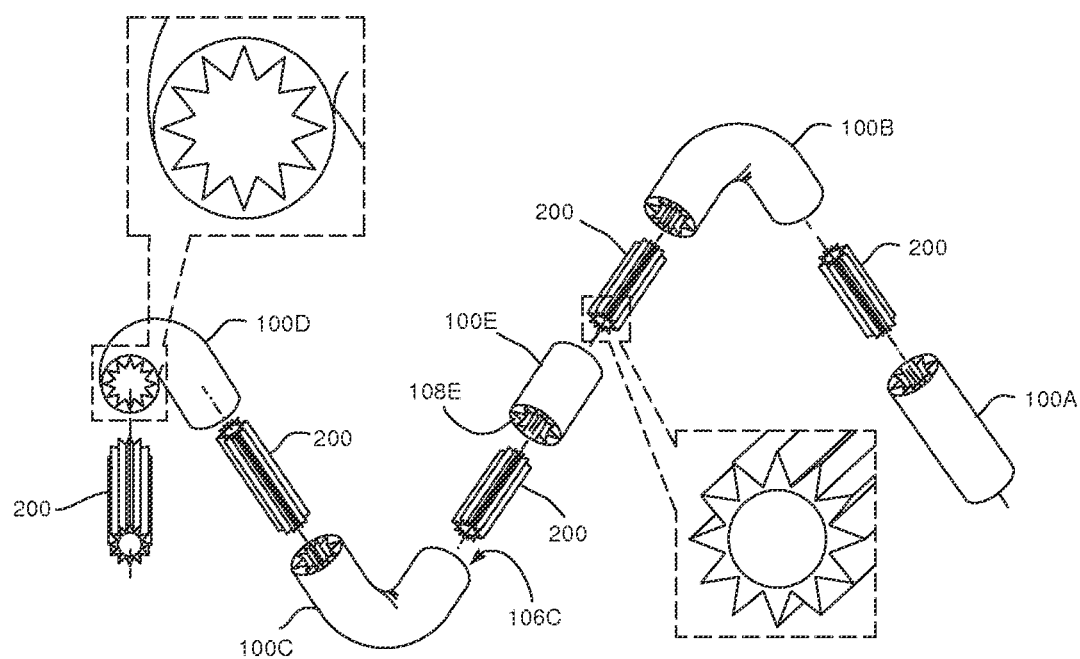
FIG. 4 is a schematic exploded view illustrating an example of modules that have been sequentially threaded onto a tube, according to an embodiment of the present invention.

FIG. 4 is a schematic exploded view illustrating an example of modules 100 that have been sequentially threaded onto tube 200, according to an embodiment of the present invention. For clarity, only sections of tube 200 are drawn in the figure; however, it will be understood that tube 200 is one element. By way of example, cylindrical module 100A, 90° elbow module 100B, cylindrical module 100E, 90° elbow module 100C, and 60° elbow module 100D have been threaded onto tube 200. It will be understood that the modules butt against each other at their plane faces. For example, face 106C of module 100C butts against face 108E of module 100E.

Returning to flowchart 500, in a sleeve application step 504, the assembled structure from step 502 is introduced into flexible insertion tube 300.

Figure 5:
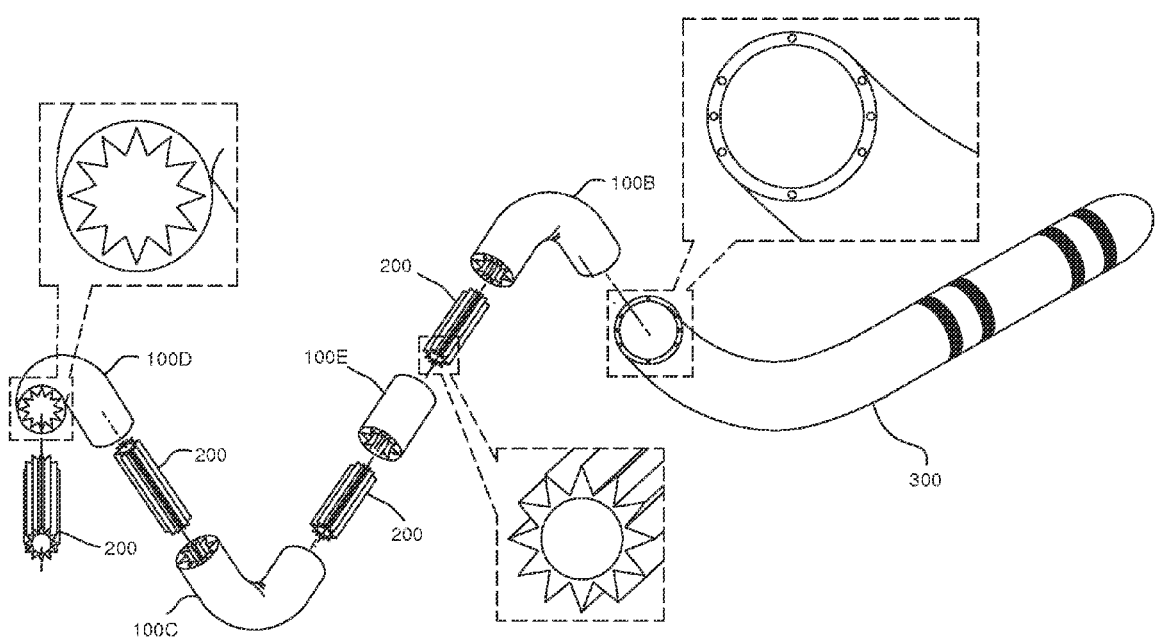
FIG. 5 is a schematic exploded view of a distal end of a catheter illustrating the insertion of modules, together with an expander tube, into an insertion tube, according to an embodiment of the present invention.
Figure 6:
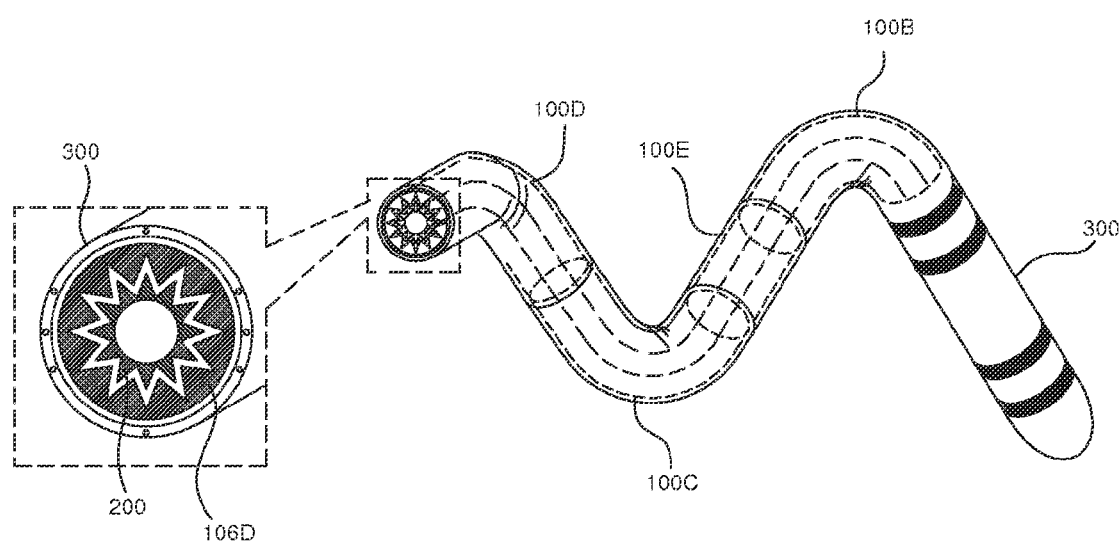
FIG. 6 is a schematic assembled view of the distal end of FIG. 5, according to an embodiment of the present invention.

FIG. 5 is a schematic exploded view of distal end 24 illustrating the insertion of modules 100, together with tube 200, into tube 300, so that the modules are contained within the insertion tube, and FIG. 6 is a schematic assembled view of the distal end after step 504 has been performed, according to embodiments of the present invention. While the grooves of tube 200 may match the grooves of the module the two sets of grooves are different in size, as is illustrated in the call-out showing face 106D and tube 200. The difference in size means that the assembly at this stage is unlocked.

In a locking step 506 an expansion element, herein assumed to comprise expansion wire 400, is inserted into expander tube 200 causing the tube to expand. Wire 400 acts as an expansion element for tube 200 by having a wire diameter larger than an unexpanded internal diameter of the tube. Typically, as wire 400 is inserted into tube 200, modules 100 that are in proximity to the end of wire 400 may be rotated to achieve a desired mutual alignment between adjacent modules, so as to achieve the shape desired by the professional (step 502). The rotation is possible since the modules terminate in plane faces, so that adjacent modules that butt against each other are able to rotate with respect to each other. If necessary, the end of wire 400 may be partially withdrawn from tube 200, so allowing modules in proximity to the end to move out of alignment, enabling realignment of the modules by reintroduction of the wire into tube 200.

Figure 7:
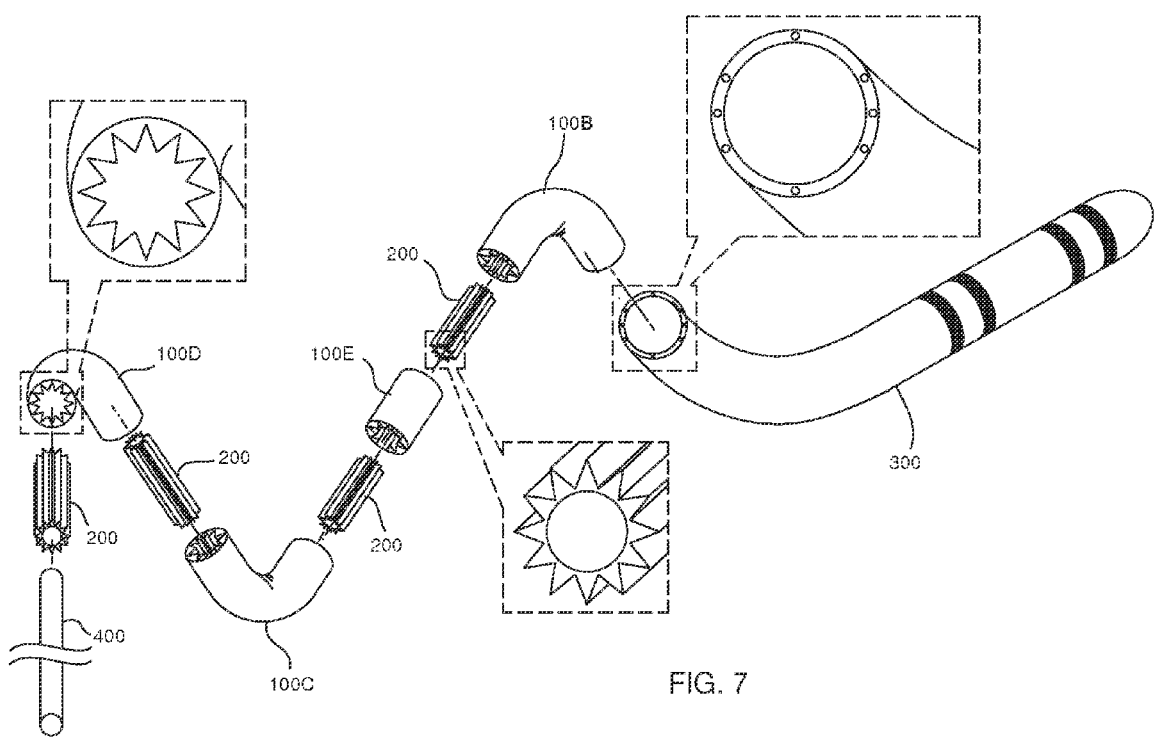
FIG. 7 is a schematic exploded view of a distal end at the beginning of insertion of an expansion wire into an expander tube, according to an embodiment of the present invention.
Figure 8:
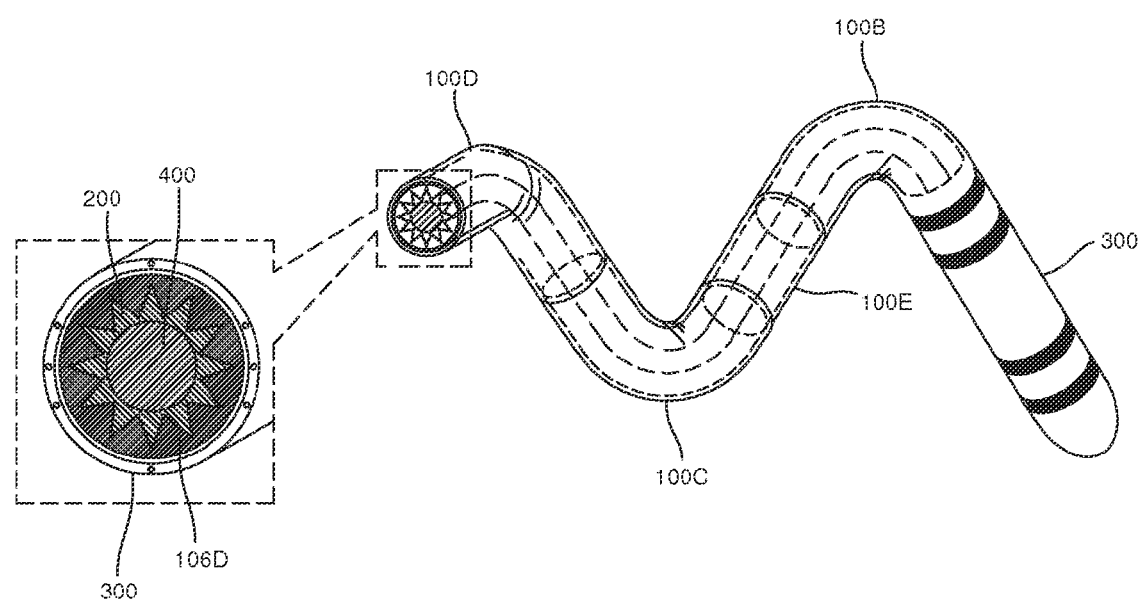
FIG. 8 is a schematic assembled view of the distal end of FIG. 7, after the expansion wire has been completely inserted into the expander tube, according to embodiments of the present invention.

FIG. 7 is a schematic exploded view of the beginning of insertion of expansion wire 400 into expander tube 200, and FIG. 8 is a schematic assembled view of distal end 24, after the expansion wire has been completely inserted into tube 200, according to embodiments of the present invention.

It will be understood that flowchart 500 is but one example of the assembly of distal end 24, and that other methods for assembly, which will be apparent to those having ordinary skill in the art, may be used. For example, tubing 300 may be slid over modules 100 after they have been locked in position by expansion of tube 200. All such methods are assumed to be comprised within the scope of the present invention.

The description above has assumed that wire 400 is inserted into tube 200 so as to effect expansion of the tube by virtue of the different diameters of the wire and the internal diameter of the tube. In an alternative embodiment, wire 400 is initially cooled so as to have a diameter less than that of tube 200, so that upon heating up the wire expands to act as the required expansion element.

In a further alternative embodiment, the expansion element may comprise liquid, such as saline solution, or gas; either of these may be injected into tube 200 to expand the tube. Thus, an expansion element that is solid, liquid, or gas is assumed to be comprised within the scope of the present invention.

While the description above refers to assembly of distal end 24, those having ordinary skill in the art will be able to apply the description, mutatis mutandis, to construction of the remainder of probe 10, including proximal end 28 sections intermediate the distal and proximal ends, and a section, such as a distal tip of distal end 24. Such will be the case if a specific shape is required for the proximal end, and/or the intermediate sections, and/or the distal tip. Alternatively, since typically only distal end 24 of probe needs to be shaped, the proximal and intermediate sections of probe 10 may be formed of a single tubular element which is inserted into tube 300 so as to contact a proximal module 100 of the distal end. The single tubular element is typically generally similar in cross-section dimensions to right cylindrical module 100A, so that it can accommodate passage of tube 200 to distal end 24. However, such a single tubular element may only be grooved at its distal end. Similarly, a distal tip of distal end 24 may be formed of a single tubular element, which may only be grooved at its proximal end.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. A probe, comprising:
a flexible insertion tube, which is configured for insertion into a body of a subject via a body lumen;
a sequence of tubular modules, which are contained within the insertion tube, each module comprising a rigid tube segment having a respective preset shape and containing internal grooves on an interior surface of the tube segment;
a flexible expander tube, which is threaded through the sequence of the tubular modules and has external grooves configured to engage the internal grooves within the tube segment of each of the tubular modules when the expander tube is expanded, so as to hold the tubular modules in mutual alignment, wherein the tubular modules are able to move out of the mutual alignment when the expander tube is unexpanded; and
an expansion element, which is insertable through the flexible expander tube so as to expand the expander tube.

2. The probe according to claim 1, wherein the mutual alignment of the tubular modules forms a predetermined shape for the probe.

3. The probe according to claim 1, wherein the flexible insertion tube comprises channels configured to accommodate at least one of cabling and fluid.

4. The probe according to claim 1, and comprising at least one electrode, formed on the flexible insertion tube, configured to acquire signals from the body of the subject.

5. The probe according to claim 1, wherein the respective preset shape comprises at least one of a right cylinder and an elbow.

6. The probe according to claim 1, wherein the respective preset shape has an axis, and is terminated by a pair of plane faces orthogonal to the axis.

7. The probe according to claim 1, wherein the expansion element comprises a wire.

8. The probe according to claim 1, wherein the expansion element comprises a fluid.

* * * * *